United States Patent
Goknar

Patent Number: 6,120,440
Date of Patent: Sep. 19, 2000

[54] DIAGNOSTIC METHOD

[76] Inventor: M. Kemal Goknar, 3873 McDivit Dr., West Bloomfield, Mich. 48237

[21] Appl. No.: 08/941,407

[22] Filed: Sep. 30, 1997

Related U.S. Application Data

[63] Continuation-in-part of application No. 07/612,816, Nov. 14, 1990, abandoned, which is a continuation-in-part of application No. 07/581,567, Sep. 11, 1990, abandoned.

[60] Provisional application No. 60/027,087, Sep. 30, 1996.

[51] Int. Cl.$^7$ .................................................. A61B 10/00
[52] U.S. Cl. .......................... 600/300; 128/923; 434/236
[58] Field of Search ........................... 600/300; 128/897, 128/898, 920, 923, 924; 434/236

[56] References Cited

PUBLICATIONS

Giannetti et al., "Development of an on–line problem–oriented system for the evaluation of mental health treatment services," Behavior Research Methods & Instrumentation, pp. 133–138.

*Primary Examiner*—Eric F. Winakur
*Attorney, Agent, or Firm*—Plunkett & Cooney, P.C.

[57] ABSTRACT

A system for psychometric analysis and diagnosis comprising an evaluation set of numbered questions. In a computerized version thereof, each numbered question is displayed on an I/O device with a rating scale and explanation thereof for the question. The clinician will then enter a rating datum for the numbered questions into the computer. When all evaluation set data is entered, the system will produce a graphic display or displays of the evaluation, and prioritize the symptomatic problem areas and assets of the current patient. The data of at least one previous patient may be retrieved and compared against the data of the current patient. Subsequent evaluation sets may be simultaneously graphed and compared with earlier evaluation sets, with the improvement or deterioration of patient status therebetween quickly quantified.

27 Claims, 6 Drawing Sheets

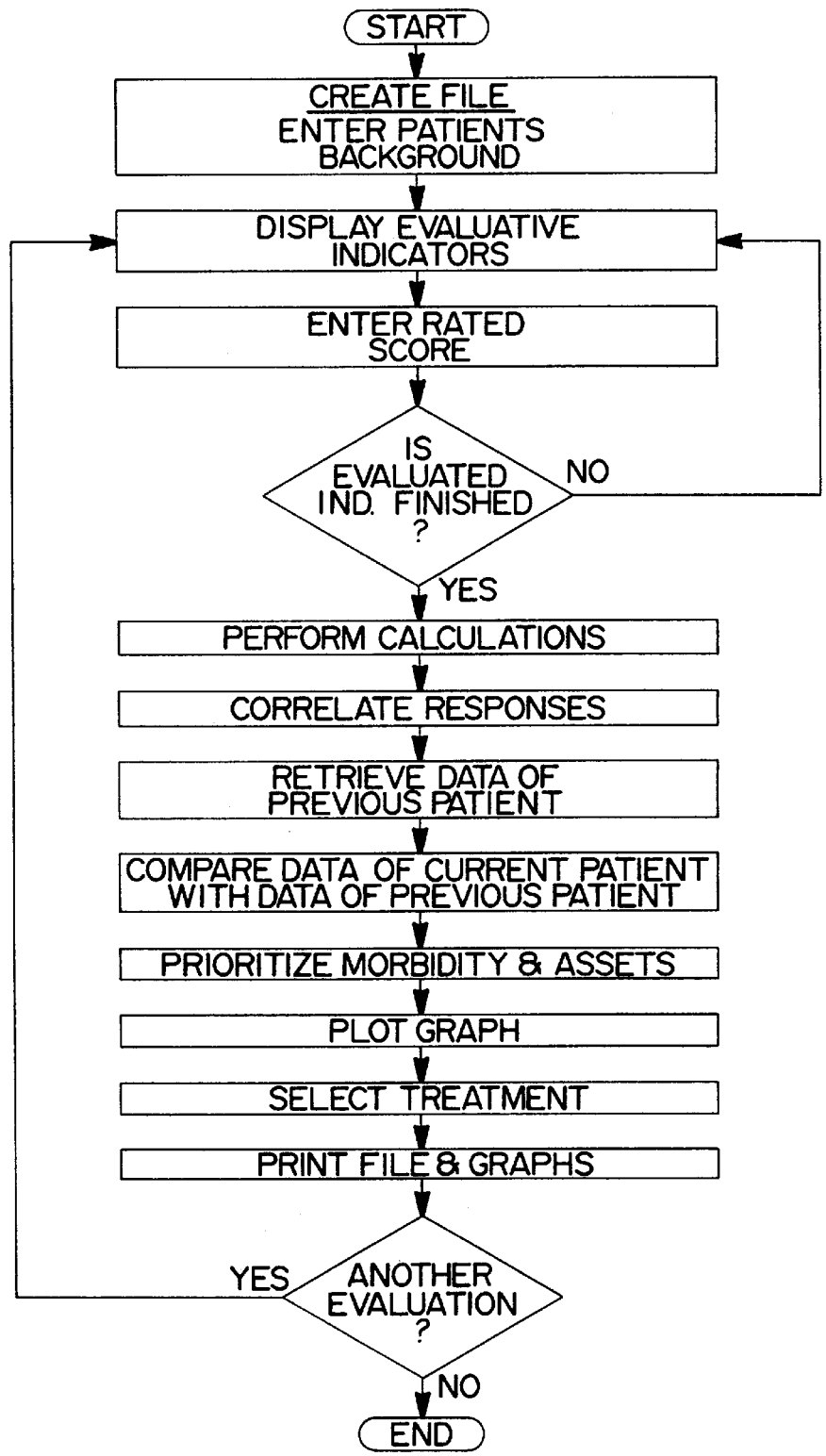
FIG IA

I. WORK-EDUCATION-CHORES

INSTRUCTION: THE RATER SHOULD SELECT THE APPROPRIATE TOPIC OF WORK, EDUCATION, OR HOUSE CHORES APPLICABLE TO THE LIFE OF THE INDIVIDUAL TO BE RATED.

QUESTIONS: HOW WOULD YOU LIKE TO RATE YOUR PERFORMANCE (ATTENDANCE, INTEREST, SKILLS, KNOWLEDGE, PRODUCTIVITY, CONSISTENCY) AND FULFILLMENT IN RELATION TO (CHOOSE ONE) WORK, EDUCATION, OR HOUSE CHORES, ETC ?.

VARIABLE: IN CASE OF AMBIGUITY, SEARCH FOR PROBLEM SOLVING ABILITY. FOR EXAMPLE, A CONFLICT WITH THE BOSS OR CO-WORKERS SHOULD BE MEASURED ON THE BASIS OF HOW MUCH IT AFFECTS ATTENDANCE, PRODUCTIVITY, INTEREST, AND CONTRIBUTIONS TO TEAM WORK.

1. EXCELLENT (CREATIVE).........SUPERIOR ACHIEVER, GREAT ORGANIZER, INSPIRATIONAL LEADER, PROBLEM SOLVER, EFFECTIVE FOR FUTURE CHALLENGES.
2. GOOD (INTEGRATIVE).........SKILLFUL, COMPETENT, ASSERTIVE, SPONTANEOUS WITH HIGH INITIATIVE, TIMELY ON PLANNING AND PROJECT ASSIGNMENTS.
3. AVERAGE (ADAPTABLE).........DOES ASSIGNED DUTIES, RELIABLE, BUREAUCRATIC AND PRODUCTIVE.
4. MILD (COMPENSATORY).........NEEDS SELF ASSESSMENT TO ADJUST TO WORK OR COPE WITH STRESSES, NEGLECTFUL, SLOW RESPONSES MAY OCCUR.
5. MODERATE (DYSFUNCTIONAL).........REQUIRES GUIDANCE, DIRECTION, OR ADVICE TO DO A REGULAR JOB. SLOPPY, LACKS INTEREST OR HAS PROBLEM WITH ATTENDANCE, CORRECTED ONLY WITH ADVICE.

6. SEVERE (IMPAIRED)..........NEEDS CLOSE SUPERVISION, MAY DISLIKE THE JOB. FREQUENTLY REPRIMANDED. PRODUCTIVITY AND ATTENDANCE IS POOR. INABILITY TO TAKE PRESSURE. MAKES THE JOB RECORD LOOK INADEQUATE, INCONSISTENT. SUCH A PERSON DEPENDS ON OTHERS OR SSI TO SUPPORT BASIC NEEDS. CAN'T RELATE TO COWORKERS OR BOSSES.

7. EXTREME (DISINTEGRATED).........UNABLE TO FUNCTION FOR ONE REASON OR ANOTHER. UNABLE TO SEE HIS OWN DIFFICULTIES, BLAMES OTHERS, VERY MUCH PREOCCUPIED IN DETAILS-IRRELEVANT, UNREALISTIC, INEFFICIENT, DISINTEGRATED.

8. CATASTROPHIC (DANGEROUS).........DANGEROUS TO SELF AND OTHERS AT WORK BECAUSE OF VINDICTIVE, IRRATIONAL CONCLUSIONS. MAY BECOME EXPLOSIVE IF PUSHED TOO FAR.

DIAGNOSTIC METHOD

CROSS REFERENCE TO RELATED APPLICATION

This application is a continuation in part of the U.S. patent application Ser. No. 07/612,816 filed Nov. 14, 1990, now abandoned, which, in turn, is a continuation in part of U.S. patent application Ser. No. 07/581,567 filed Sep. 11, 1990, now abandoned, as well as a completion application of copending Provisional Application Serial Number 60/027,087, filed Sep. 30, 1996, the disclosures of which are incorporated herein by reference.

BACKGROUND

1. Field of the Invention:

The present invention relates generally to psychometric studies. More particularly, the present invention relates to a computer program enabling a mental health clinician, of less skill than an M.D., D.O., or Ph.D., to perform psychometric evaluations, obtain meaningful symptomatic analysis, and recommend courses of treatment from the evaluation.

2. Discussion of the Related Art:

Heretofore, psychological evaluations and diagnosis were largely conducted by letting the patient discuss his feelings in a monologue, either unguided or guided by the mental health practitioner. From this monologue, the practitioner ascertains symptoms of psychological impairment and/or areas of adequate psychological functioning, i.e., a picture of the mental health of the patient.

From these symptoms the practitioner decides on a course of treatment for the symptoms of the patient.

Further, such a traditional approach suffers from a number of shortcomings, among which are:

(1) the length of time necessary to develop an adequate diagnosis;
(2) a high level of training and skill, e.g. an M.D., D.O., or Ph.D. is ordinarily required of the practitioner to conduct such an evaluation;
(3) the evaluation process lacks uniformity and reliability when conducted either by a single practitioner or, especially, by different practitioners; and particularly as applied over a series of evaluations;
(4) the evaluation process is not readily understood by patients; and
(5) the evaluation is not readily quantifiable in numerical terms or easily displayed in a graphic format.

Some tools exist to address some of these deficiencies, in part. A magazine article authored by J. Hedlund and B Vieweg which discusses computer usage in psychiatric practice can be found in the April 1988 issue of Psychiatric Annals on pages 217–227, and this article contains an extensive list of references.

Although discussing pioneering efforts and work accomplished so far, two of the findings of the above-identified magazine article are of note here: (1) there has been surprisingly little development of new psychological testing designed to take advantage of the special capabilities of the computer, and (2) the danger that automation of the testing will increase the problem of invalid interpretation by untrained people. This points to the need in the art for a well defined test, of general applicability, that calls for responses and reduces the likelihood of misinterpretation of results, while taking advantage of the power of computers of today, especially office and personal computers.

A well-known work in the field of mental health as is the *Diagnostic and Statistical Manual of Mental Health*, American Psychiatric Association, 3rd ed. rev. (1987) and 4th ed. rev. (1994) (hereinafter abbreviated DSM). This text contains lists of diagnostic categories and criteria, with a scale, weighted 0–6, to score responses. The DSM system does not quantify severity in a measurable term except in an estimated GAFS score nor does it address a functional level of a healthy individual. Grading on the DSM scale, while using the same spread, does not have the same severity from response to response. That is, a grade of 4 in one category does not correspond to a grade of 4 in another category. Therefore, an overall consistency is not achieved by the DSM system, hindering significance in diagnosis and treatment. Other clinical assessment tools currently exist, particularly the Minnesota Multiphasic Personality Inventory (MMPI), Global Assessment Scale, Mini Psychiatric Scale, the Hamilton anxiety scale, the Hamilton Depression Scale, and the Beck Inventory. Like the *Diagnostic and Statistical Manual*, the effectiveness of these devices is limited: the GAS, and Mini Psychiatric Scale are too broad in scope; and the Hamilton and Beck Inventory are too restricted in specificity. Neuropsychological testing is generally very specific in scope, as available in the prior art. Thus, these tools are therefore only of limited assistance in general situations, or are effective only in specialized circumstances; they do not cover the variety of individual differences in health or in pathological adaptation.

A need therefore exists in the art for a concise, easily utilized, consistent and readily graphed and understood psychometric and diagnostic method, and particularly for such a method which is easily accessible and manipulatable, and which has its entire stock of diagnostic evaluations readily available and comparable with each other.

SUMMARY OF THE INVENTION

The present invention solves the aforementioned problems of the traditional approach of psychological observation, by providing the system of psychometric analysis and diagnosis, preferably utilizing a computer having a CPU, Input/Output devices, memory, and operating systems therefor, comprising the steps of (a) storing data representing a list of numbered evaluative indicators in a computer memory;
(b) displaying the evaluative indicators on an Input/Output device;
(c) entering a numerical datum score of patient performance level, corresponding to a response of a patient for each evaluative indicator, with an Input/Output device into the computer memory, the total data representing an evaluation;
(d) calculating graph coordinates within a CPU using the numerical data on a first axis and evaluative indicators on a second axis;
(e) displaying a graph of the coordinates on an Input/Output device;
(f) evaluating the numerical data within the CPU to determine the psychiatric symptoms and assets of the patient;
(g) matching the evaluated data with treatment plan options stored in the computer memory to select a treatment plan for the patient; and
(h) displaying the selected treatment plan on an Input/Output device.

It will be realized by the artisan that the majority of the system functions described herein may be performed manually by a mental health practitioner with appropriate forms and the like. Such a use of the system, while much more labor intensive than the computerized versions described herein, may be the preferred application in certain environments, and is meant to be encompassed as an embodiment of the present invention. The system of the present invention is given the designation of the Goknar Master Assessment and Progress Scale, abbreviated MAPS.

Generally, a first evaluation will be conducted by scoring a complete list of evaluative indicators to form a whole, or global, psychiatric profile, or evaluation, of the patient. The indicators are grouped into the diagnostic categories Function, Cognition, Emotion, Behavior, Personality, and Risk Factors. A like number of indicators are scored for each category.

Scoring scale explanatory text accompanies each indicator providing consistent rating criteria for the numerical datum. The scale goes from a number one which is an excellent rating, to a number eight, which is an extreme or critical rating. It is an advantage of the present invention that a standardized scale is provided, in which responses from one category may be compared to responses from another category.

The scoring scale for evaluating an answer of the patient was developed using the reference of what previously existed in the art as a starting point. The Diagnostic and Statistical Manual scale of 0–6 was modified in two important ways: (1) these DSM negative response indicators 1–6 were correlated to 3–8 on the MAPS rating scale according to the present invention; (2) positive health factors, or assets, were included at rankings 1 & 2. Thus, the MAPS scale runs from 1, a superior, beneficial quality, to an 8, a catastrophic dysfunction, indicating a dangerous characteristic.

It should be noted that while the MAPS scale is based loosely upon the DSM scale, this was done for ease of reference for many practitioners. Specifically of note is that MAPS avoids the drawbacks of DSM and other available systems by the careful composition of each question to allow for a "global" or total psychological picture of a patient. This is achieved by correlation of the question, to compliment or contrast another question, thus revealing nuances and insights which allow for a most suitable diagnosis and priorities in treatment.

The scale also points out the versatility of MAPS: it can be used effectively on virtually any patient. Not confined to specific disorders, it can diagnose diverse ailments, or identify a healthy individual, and rank his or her level of adaptation. The inclusion of assets in the considerations affords this. The scoring is balanced to account for four components important in revealing pathology: (1) global score: (2) individual score on any given question; (3) cluster scores in six cluster categories; (4) Goknar Inventory Analysis, which breaks down total patient behavior into components thereof, and assigns a percentile rating to each of the components.

The above-identified Goknar Inventory Index defines, with mathematical precision, the acute, subacute, chronic signs (in percentile) and the average and/or better than average responses (assets), again in percentile figures. The Goknar Inventory Index also categorizes the percentile of dangerous, extreme, severe, and marginal symptoms, comparing these with the average and/or asset results.

Once the evaluation is complete, i.e., all data are entered into memory, the system requires that the operator, with or without the aid of the computer, perform the following functions: total the data to produce an overall score; figure mean scores for each diagnostic category; display the results in graphic form, in line graph or bar graph form, or both; correlate individual indicators into psychiatric symptom subsets, and calculate the data therein and prioritize the symptoms in priority of morbidity and psychological asset strengths of the patient. The computerized system will perform the calculations according to algorithms conducted in the CPU on the data drawn from memory.

The calculated data is compared and matched to various treatment options to select the treatment option or options most nearly fitting the psychological profile of the patient. The treatment option is then displayed, in the computerized embodiment on an Input/Output device if desired by the practitioner, or is recorded for later reference.

Subsequent evaluations may be conducted with the entire list of indicators or may only include those indicators relevant to the psychological diagnosis of the patient and/or treatment plan.

The graphs of subsequent evaluations are displayed concurrently with previous evaluations to present an easily understandable picture of the psychological improvement or deterioration of the patient. Subsequent evaluation data are also calculated against selected previous evaluation data to indicate percentages of psychological improvement or deterioration. Thus the present invention also is a means for predicting future psychological improvement or deterioration of the patient.

Room for practitioner comments is provided for in each indicator datum location, as such comments will often be necessary in developing a patient psychological profile. All raw and calculated data is preserved in each file of the patient for later reference. The labeling of each evaluation is provided for in the system, to enable the practitioner to quickly recall and/or compare various evaluations. Preferably, an individual "best performance" evaluation is also conducted and entered into the file of the patient as a goal for patient treatment results.

It is an object of the present invention to provide a standardized, systematic, diagnostic method in which ratings from one diagnostic category can be related and compared quantitatively with rating from another diagnostic category. In addition, the present invention provides the clinician to predict which disorders may occur if the patient functions at a continued level.

It is an advantage of the present invention that the numerical rating of a patient response to any given evaluative indicator can be related and quantitatively compared to a standardized rating scale.

It is a feature of the present invention that total patient behavior is statistically evaluated and broken down into components thereof, with a percentile rating being assigned to each component.

The system of the present invention additionally provides a clinical assessment which lists a set of dysfunctions, physical or psychological, upon the responses of the patient. Additionally, the system provides a comparison between the results of the current patient and the results of other patients who was administered the same test.

Alternatively, the present invention provides a more sensitive rating system by adding more diagnostic categories, giving a finer definition of each score.

Other attendant advantages will be more readily appreciated as the same becomes better understood by reference to the following detailed description and considered in connection with the accompanying drawings, in which, like reference numerals designate like parts throughout the figures.

BRIEF DESCRIPTION OF THE DRAWINGS

FIG. 1A is a block diagram of psychometric operating procedures;

FIG. 3 illustrates a sample evaluative indicator as displayed on a video monitor.

DETAILED DESCRIPTION OF THE PREFERRED EMBODIMENT

Figure 1:
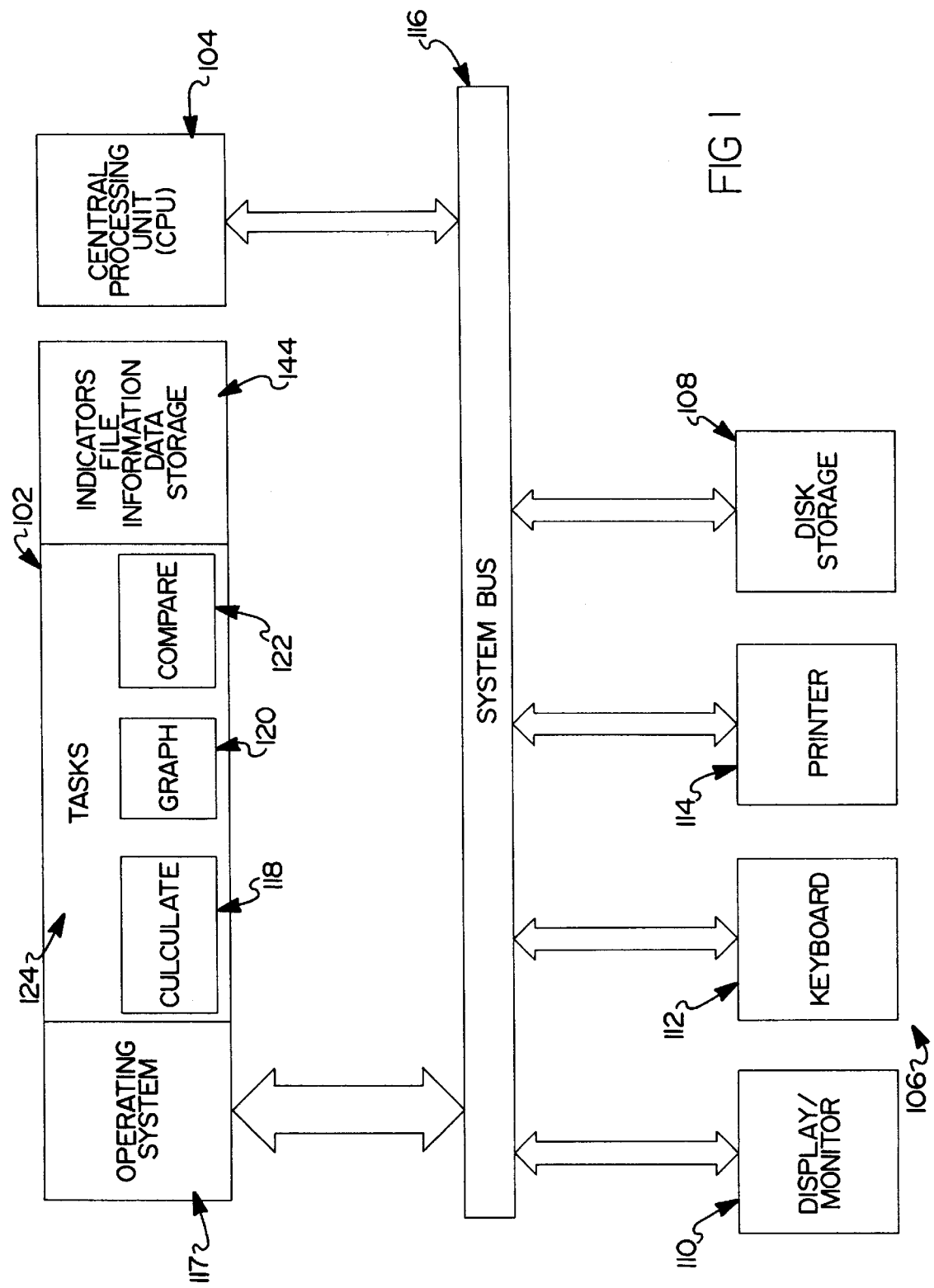
FIG. 1 is a block diagram of a system incorporating the present invention.

Referring to FIG. 1, a block diagram representation of a system incorporating the present invention is shown. The system will include such standard hardware elements of computer functioning as a memory 102, a central processing unit or CPU 104, and various Input/Output devices 105 such as may include: a disk storage unit 108 or computer/user interfaces such as a video monitor 110, a keyboard 112, and a printer 114. All the components are connected through a system bus 116 to allow communication between the components.

A diagnostic program of computer software, an exemplary portion of which is attached to Provisional Application 60/027,087 as Appendix A, and which is incorporated herein by reference, is loaded into the memory 102 and/or retained in part in the disk storage 108 to be called as needed. The program contains instruction sets of data representing operating systems or procedures 117 to run the program and perform recurrent management tasks of the program such as data entry operations, and the like, and is retained in the memory 102 for quick access. A further discussion of the software will take place hereinbelow. Smaller instruction sets or those needed for occasional program tasks 118, 120, 122, 123 are labeled application systems 124 and may be placed in the memory 102 from the disk storage 108 as needed when called for by the operating system 117.

Figure 2:
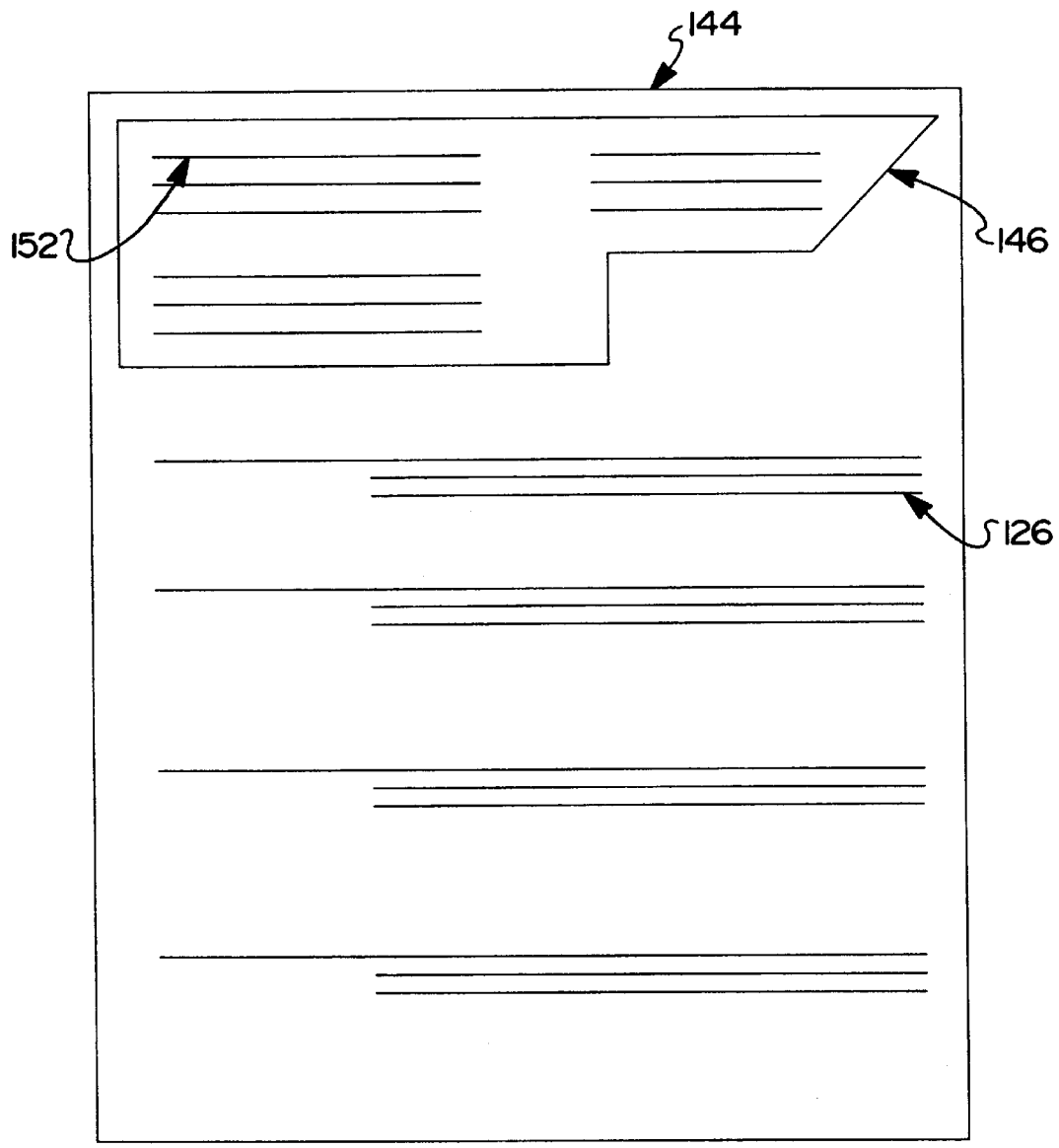
FIG. 2 illustrates a generalized patient file according to the present invention.

As seen in FIG. 2, the diagnostic program contains operating systems which help an operator create a file 144, which is a memory or data grouping containing all data relevant to a particular patient. The file header 146 contains necessary patient demographic information and evaluation information such as dates, name of the evaluator, etc. Entry of this header data into computer memory by operation of the keyboard 112 creates a patient file capable of holding all subsequent evaluation data for the patient. Alternatively, data entry may take place by scanning a form which has been filled out by the patient or subject with whom the system is being used. By using a commercially available scanner with character recognition software, the contents of the form i.e., the text written thereupon may be read into the memory of the computer. The form may be substantially similar in its layout to the file 144 which is depicted in FIG. 2. The use of a scanner recognition software is well known in the art, and may provide for substantially simpler use of the system 10 of the present invention.

Also loaded in the memory 102 are data representing specific responses of a patient to a series of evaluative indicators 126, which are displayed as textual reference, an illustrative example of questions and the available responses is shown in FIG. 3, which are intended to be displayed on the video monitor 110. The indicators 126 are components of individual diagnostic factors concerning the physical, mental, and environmental state of the patient. The indicators 126 are individually numbered and grouped into six diagnostic categories of Function, Cognition, Emotion, Behavior, Personality, and Risk Factors, or the patient. In the preferred embodiment, there are eight indicators for each diagnostic category for a total of forty-eight indicators. An illustrative sampling of the forty-eight evaluative indicators which are included in Provisional Application 60/027,087 as Appendix B.

It should also be appreciated that the answers to these questions may be entered into the computer via a scanner and optical character recognizing software, just as is available with respect to the data form mentioned herein above. Further, it should be noted that a preferred and common usage of the present system will involve computer systems running the popular format Windows, produced by Microsoft. The present system is capable of use in the Windows 3.1 version, as well as one the newer Windows 95 version. It if foreseen that the present system can be modified to perform on newer versions of Windows, or in other similar environments, such as Apple Macintosh products, and the like.

Preferably, the clinician, who administers the questioning to determine the appropriate patient response for each evaluative indicator, will have at least a 4-year college degree in an area relevant to mental health, as well as one year of clinical psychiatric experience, and 24 hours of training in the application of the MAPS system. The system of the present invitation is not intended for use by amateur or unskilled personnel.

As seen in FIG. 3, the displayed screen 135 includes of a title 136 for the diagnostic factor of the evaluative indicator 137, a brief exposition 138 of the title 136 detailing what is to be rated, and a rating scale explanation 140 to provide guidance to the evaluator, or clinician, in selecting a numerical datum score for the indicator according to a response given by a patient, the datum, which is then placed in a datum space provided there for retrieval by the evaluator through operation of the keyboard 112. The datum is retained in the memory 102 for later processing, as further explained below. An evaluation involves entering data corresponding to responses obtained for all indicators scored in a particular rating session; whether all forty-eight indicators, that is, a complete evaluation, or a lesser amount thereof, which is a partial evaluation; plus supplemental comments on the individual evaluative indicator patient performance entered into the memory 102 by the evaluator.

The clinician may pose the questions to a patient and write down the responses on a form which may then be read into the computer via a scanner as described herein above.

Figure 4A:
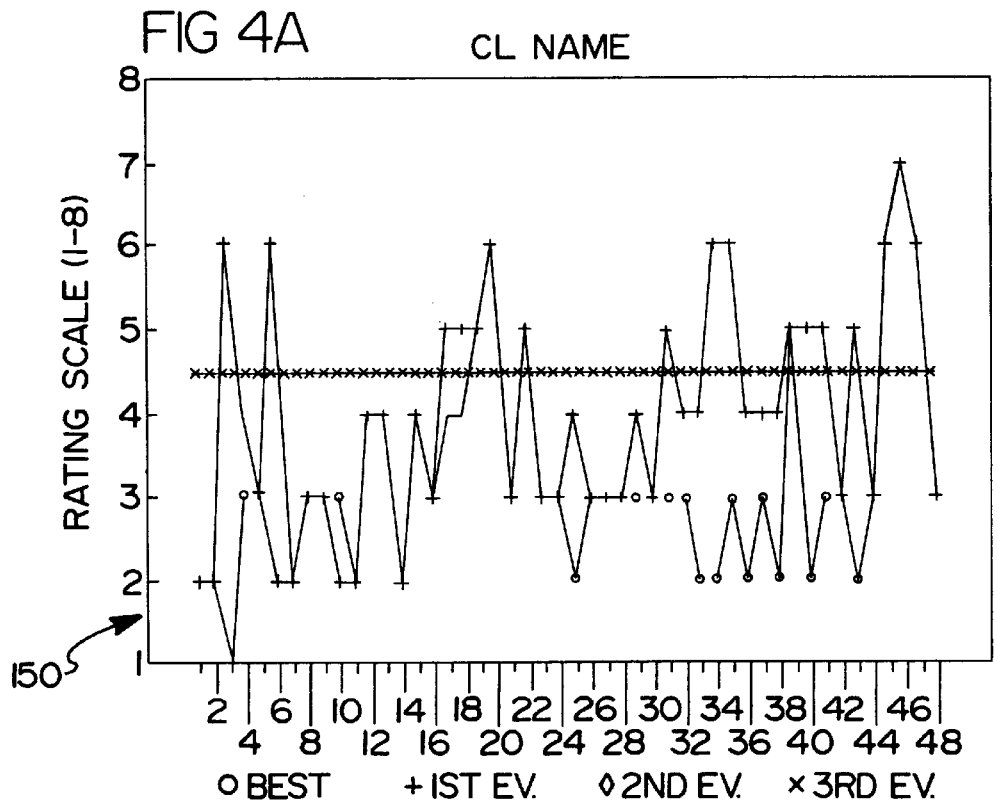
FIG. 4 illustrates a graphical representation of a file according to the present invention.
Figure 4B:
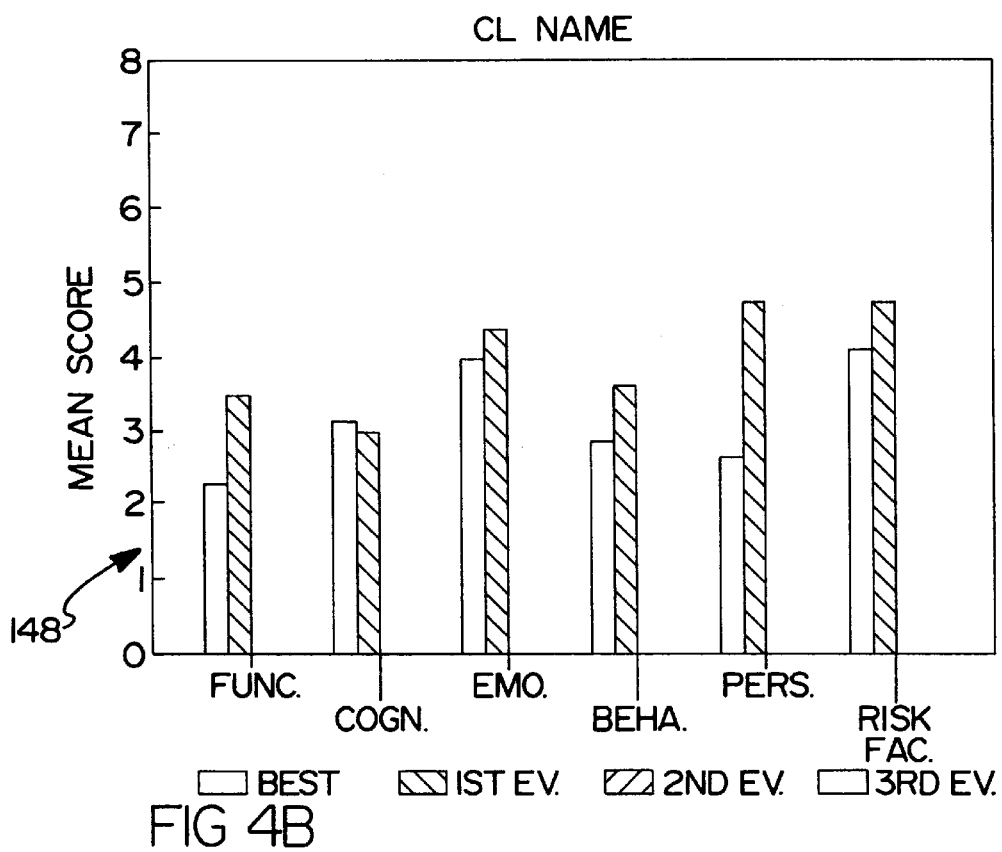

Once all evaluation data has been entered into the memory 102, via the keyboard or a scanner, algorithms contained within the applications or operating systems of the memory 102 will direct the CPU 104 in calculating graph coordinates for graphing of the evaluation data against the diagnostic category as seen in the bar graph 148 of FIG. 4, or against the numbered indicators, as seen in the line graph 150 of FIG. 4. The graph coordinates will then be sent out to the printer 114 and/or monitor 110, or other suitable Input/Output device, for displaying the graph(s) 148, 150 to provide a graphic illustration of the evaluation results, the graphic form being readily understandable and viewable by both the patient and the mental health practitioner.

As seen in FIG. 1, the evaluation numerical data in the memory 102 is then calculated by the CPU 104 according to algorithms contained in the operating systems 117 to derive total scores and mean scores for each diagnostic category and the calculation results displayed on a suitable Input/Output device 106. The mean scores may further be used to determine bar graph coordinates for the display of a bar graph 148 plotting the mean scores against each diagnostic category. The data may also be used to calculate the Goknar Inventory Index according to predetermined algorithms stored in memory 102.

Additionally supplied by the present system is a means for predicting for the future psychological improvement or deterioration of the patient. This is accomplished by altering the numerical ratings supplied by the clinician. A full discussion of this feature of the present invention follows herein below.

The special nature and design of the Goknar Inventory Index should be noted here, so that its contribution to the art can be appreciated. The Goknar Inventory Index allows for numerical representation of the clinical symptoms and severity levels of the patient, according to information received from the patient in his responses, as an index of clinical significance. By being able to represent these concepts mathematically, the Goknar Inventory Index achieves significant advantages over the previous systems.

First, the index summarizes the functional level of an individual at the time of evaluation. This provides baseline information and can be compared with the Goknar Inventory Indexes of other examinations, giving a comparative clinical picture of a progress or illness of the patient from stage to stage, illustrating dynamically the improvement or deterioration of the patient.

In addition, the Goknar Inventory Index allows for categorization of the extent of the symptoms and assets of a patient, and allows for quantitative breakdown of the behavior of the patient into components. The Index shows where a patient, on a percentage basis, scores for assets, normal or average behavior, and various degrees of dysfunction, from chronic, up through subacute, to acute symptoms.

Further, extreme and dangerous behavior is categorized. This is quite valuable, as proper application of the MAPS system will show patients who should be institutionalized for their own good, as well as the good of society. It also will point out trends in this direction and point out applicable treatment options. Thus, the Goknar Inventory Index is a major advance in the art and, as part of MAPS, allows a professional having less training than an M.D., D.O., or Ph.D. to achieve useful results after each evaluation, with interpretation showing current status as well as the progress of the patient.

In a professional format, the Goknar Inventory Index is derived by starting with a first or baseline evaluation, in which the interviewer obtains responses from the patient for all 48 questions, as seen, for example, in Appendix B, in all the six functional areas previously identified. The response to each question is rated on a scale of 1–8, with a rating of 1 representing the best condition and 8 representing the most extreme catastrophic or dysfunctional condition. The response received are then related, firstly to the categories of average, and assets, and secondly, to a severity ranking of dangerous, extreme, severe, marginal and average/assets. In each case, a percentage is indicated for each category.

The answers are evaluated according to a rating scale, which corresponds to the 1–8 scores. A rating of Dangerous equates with an 8 rating and denotes a dangerous situation, such as homicidal, suicidal, or catastrophic condition. This requires documentation.

A rating of Extreme equates with a 7 score, which denotes extreme problem such as unpredictability, disintegration, and the like. A rating of Severe equates with a score of 6, and indicates a severe condition or psychotic responses. Both an Extreme rating and a Severe rating also requires documentation. A rating of Moderate corresponds with a score of 5. A rating of Marginal corresponds with a score of 4. A rating of Average corresponds with a score of 3. Scores of 2 or 1 are given a rating of Asset, above average or superior, which also requires documentation.

After the complete evaluation is obtained, the total number of ratings with a score of 3 are divided by the total number of questions to determine a percentage of average responses. This number is 48 in full evaluation. In a like manner, the total number of responses with a score of 2 to 1 is divided by the total number of indicators to determine a percentage of assets of the patient. In the initial baseline evaluation, no rating is make of acute, subacute, or chronic behavior because this only has relevance in a series of evaluations in terms of a change in behavior. The initial percentage ratings for average responses and responses indicating assets are listed under the heading Episode. Under a separate heading of Severity, a listing is made for the percent of answers corresponding to dangerous, extreme, severe, marginal, and average/asset responses are calculated in a manner similar to that described above for average and assets. Under the heading of Severity, average and asset responses, that is, ratings with a score of 1–3, are lumped together in the category of average/asset. The categories of severity may be rated in the initial baseline interview, and do not require a change over time.

If is to be noted that a second embodiment of the present invention provides for a more sensitive rating system. Additional categories are added, with successive additional numerical ratings, i.e., 9, 10, etc. The additional categories gives a finer definition of each score. This in turn allows for the more particular ratings to be used to identify more particularly dysfunctions or assets. Accordingly, it is to be noted that the cumulative scores are increased under this second system.

After a period of time which the evaluator feels appropriate, a second interview is conducted. Such a period may last from as little as a few days up to a period of weeks, ranging from three to six months. The period could be even longer, depending upon the individual patient. In the second interview, the patient gives responses to each of the identical evaluative indicators which were rated in the first interview. The new responses are then evaluated in the same manner as the initial responses. This will show changes in the various categories, either relatively stable with minimal changes, and improvement in the condition of the patient, or possible a deterioration in the condition of the patient.

In a preferred embodiment hereof, in the initial evaluation or at another time, the patient provides information on his or her best period of functioning within the last five years, and provides responses to each of the evaluative indicators rating the best performances of that patient in the last five year period. In the discretion of the evaluator, if a particular situation warrants going back beyond five years for a rating of the best performance of the patient, this may also be done. A period beyond five years would indicate a chronic condition.

An additional scale is used to evaluate changes in the patient from the response rating for the best performance in the past five year period. Three ratings are used in this scale: acute, subacute, and chronic. Questions with a 4 or more rating point increase between the response corresponding to the best performance period and the response of the current evaluation, or with a 4 or more rating point difference between evaluations, are classified as acute. Questions with a 3 point increase between the best evaluation and the current evaluation, or between subsequent evaluations, are classified as subacute. Questions with a 2 or 1 point increase, or no change, between the best performance period in the current evaluation period, or between subsequent evaluations, are classified as chronic.

The categories of acute, subacute, and chronic are rated for any period which is increased from the best period and for every subsequent period, in a manner similar to that outline above for average and asset ratings.

In the second embodiment of this system, the additional scale may also be extended, as the number or rated systems has been so extended.

The evaluated data may then be compared against known treatments for similar data profiles and a treatment selected from memory for the patient file and displayed on an Input/Output device. For instance, a total score of over 230 may be criteria for admitting a patient to a hospital, scores of 190–229 may indicate admission to a hospital day program, and scores of 110–189 may indicate a need for outpatient therapy. In chronic conditions these scores may move upward.

Subsequent evaluations, either complete or partial, are conducted with operating systems tailored to subsequent iterations of patient evaluations and, upon completion, are entered in the file of the patient. The subsequent evaluation data can be graphically displayed together with earlier evaluations on an Input/Output device to produce a readily understood picture of the improvement or deterioration of the patient in each selected diagnostic category.

Additionally, as embodied in the present system, there is provided a means for predicting for future improvement and/or deterioration of a patient. This is depicted as the predict task 123 of FIG. 1. To accomplish this, the survey results obtained from the patient, that is, the numerical results, are artificially inflated to simulate a deterioration in the condition of the patient, or reduced to simulate functional improvement. The clinician may view these "new" results to see what may happen to the patient regarding possible new disorders or curing of old disorders, as a patient improves or deteriorates.

The predicted results may additionally be printed in graphical form so a clinician may show the patient what might occur, what disorders might manifest or cease if the patient improves or deteriorates their function, as it relates to the rated questions. With the second embodiment of the present system, it is understood that finer gradiations and additional rating categories will provide even greater opportunity for the skilled clinician to properly diagnose the patient and the illness(es) present.

The clinician may also predict what disorders may occur if the patient functions at an improved or deteriorated level in any of the six diagnostic categories. To accomplish this, the answer to each question which falls under a selected diagnostic category, rated as 1–8, may be inflated or reduced to simulate the improvement or deterioration of a patient in that one category. Numerical percentages or improvement in the mean score of each selected diagnostic category may also be calculated and displayed. Again, in the second embodiment of this system, disorders are more easily discerned in the increased sensitivity index.

In use, the operator will load the software into the memory 102 by means of a disk (not shown) in disk storage 108 and call up a file header 146. File data will be entered into memory 102 according to the labels 152 on the header and a patient file 144 is thereby created.

The data representing patient responses to the evaluative indicators will be serially withdrawn from memory 102 and displayed in operator intelligible form on the video monitor 10. The operator will then enter a numerical datum score for each displayed indicator by means of the keyboard 112, or scanner, using the displayed scale explanation 140 for help in rating, if needed.

It will be appreciated that due to the format of the present diagnostic system a relatively unskilled mental health practitioner, such as a clinician having a 4-year degree, rather than an M.D., D.O. or Ph.D. can perform the evaluation and obtain consistent and accurate results.

Once the indicators have been scored or rated, the system will graphically an numerically display the calculated and analyzed results of the raw data as discussed above. Because the data is quantified on a numerical scale, it is readily understood and appreciated by both the practitioner and the patient. This will lead to decreased patient anxiety over the process and increased patient participation in the psychological diagnosis and treatment.

The system of the present invention additionally provides a clinical assessment which will list a set of dysfunctions, whether physical, social, or psychological, which may be present upon the responses of the patient. This clinical assessment is shown in the example which follows hereinbelow.

A clinical assessment may be produced for a predicted improvement or decline in any of the six categories, or for individual questions as well. In this way, a clinician can see, by the assessment, what dysfunction may manifest or cease based upon the improvement or decline of a patient. This can help the clinician choose appropriate treatments and an appropriate timetable for the application.

In addition the system provides not only a comparison of the individual with himself/herself in relation to past, present, and progress stages, but also a comparison with other individual(s) who took the same test. Especially in marital, couple, family relationships such comparison leads to a scientifically sensible analysis of the similarity and differences, (compatibility profile), crucial in the treatment and resolution of the conflict. System specifically programmed to provide on going information on those lines covering past, present, progress stages, maturational levels of the partners to help them work together in their difficulties, or support each other on their strongest point.

Having, thus, described the invention, what is claimed is:

1. A method for psychometric analysis and diagnosis comprising:

(a) creating a current patient file for a current patient in which to record patient psychiatric symptoms and evaluations;

(b) displaying a series of numbered evaluative indicators;

(c) recording a numerical datum score of the current patient performance level for each evaluative indicator in a patient file, the total data representing an evaluation;

(d) calculating graph coordinates using the numerical data of the current patient performance level on a first axis and evaluative indicators on a second axis;

(e) creating a graph from the calculated coordinates in the current patient file;

(f) retrieving available calculated graph coordinates from at least one previous patient performance level for each evaluative indicator in at least one previous patient file, the available calculated graph coordinates including the numerical data of the at least one previous patient performance level on a first axis and evaluative indicators on a second axis;

(g) altering the numerical data of the current patient performance level after retrieving the available calculated graph coordinates of the at least one previous patient performance level for each evaluative indicator;

(h) evaluating the numerical data of the current patient to determine the psychiatric symptoms and assets of the current patient;

(i) comparing the numerical data of the current patient with the numerical data of the at least one previous patient;

(j) matching the evaluated data with treatment plan options to select a treatment plan for the current patient; and (k) recording the treatment plan in the current patient file.

2. The method of claim 1, wherein the altering numerical data of the current patient comprises:

inflating the numerical data of the current patient.

3. The method of claim 2, which further includes predicting the psychiatric symptoms and assets of the current patient, after inflating the numerical data.

4. The method of claim 1, wherein the altering numerical data of the current patient comprises:

deflating the numerical data of the current patient.

5. The method of claim 4, which further includes predicting the psychiatric symptoms and assets of the current patient, after deflating the numerical data.

6. The system of claim 1, wherein evaluating the numerical data of the current patient comprises:

(a) altering the numerical data of the current patient; and (b) predicting the psychiatric symptoms and assets of the current patient as to the altered numerical data.

7. The method of claim 6, wherein altering the numerical data of the current patient comprises:

inflating the numerical data of the current patient.

8. The method of claim 6, wherein altering the numerical data of the current patient comprises deflating the numerical data of the current patient.

9. The method of claim 1, wherein subsequent evaluations are entered into the memory by use of an Input/Output device for the same patient.

10. The method of claim 1, wherein the evaluative indicators are grouped according to diagnostic categories.

11. The method of claim 1, wherein the steps (a)–(i) are performed for subsequent evaluations and recorded in the current patient file.

12. A method of psychometrically analyzing and diagnosing a patient, which comprises the following steps:

(a) creating a patient profile comprising indicators which represent personal and background information about the current patient;

(b) obtaining responses from the patient concerning his best psychological functioning period within the preceding five years;

(c) rating the responses;

(d) adding indicators corresponding to the responses to the current patient profile;

(e) obtaining additional responses from the patient concerning the present psychological functioning of the current patient;

(f) rating the additional responses;

(g) adding indicators corresponding to the additional responses to the profile of the current patient;

(h) analyzing the indicators corresponding to the best period of psychological functioning and the current level of psychological functioning of the current patient;

(i) adding indicators to the profile of the patient corresponding to the analysis of the best period of psychological functioning and the current level of psychological functioning of the current patient;

(j) retrieving available indicators of at least one previous patient, the indicators corresponding to the best period of psychological functioning and the analyzed level of psychological functioning of the at least one previous patient;

(k) altering the indicators corresponding to the best period of psychological functioning and the current level of psychological functioning of the current patient after retrieving the available indicators of the at least one patient and before the comparing the indicators corresponding to the best period of psychological functioning and the current level of psychological functioning of the current patient against the indicators corresponding to the best period of psychological functioning and the analyzed level of psychological functioning of the at least one previous patient;

(l) comparing the indicators corresponding to the best period of psychological functioning and the current level of psychological functioning of the current patient against the indicators corresponding the best period of psychological functioning and the analyzed level of psychological functioning of the at least one previous patient;

(m) printing at least some of the indicators corresponding to the profile of the patient;

(n) graphically representing at least some of the indicators corresponding to the analysis of the best period of psychological functioning, and the current level of psychological functioning and the rated responses of the best period psychological functioning of the patient and the current level of psychological functioning;

(o) performing analysis to select a treatment;

(p) adding indicators corresponding to the selected treatment to the profile of the patient, and (q) printing at least some of the indicators corresponding to the selected treatment of the patient.

13. The method of claim 12, wherein the altering the indicators corresponding to the best period of psychological functioning and the current level of psychological functioning of the current patient further comprises inflating the indicators of the current patient.

14. The method of claim 13, which further includes predicting at least one future level of psychological functioning and the psychiatric symptoms and assets of the current patient after inflating the indicators.

15. The method of claim 12, wherein the altering the indicators corresponding to the best period of psychological functioning and the current level of psychological functioning of the current patient further comprises deflating the indicators of the current patient.

16. The method of claim 15, which further includes predicting at least one future level of psychological functioning and the psychiatric symptoms and assets of the current patient, after deflating the indicators.

17. The method of claim 12, wherein analyzing the indicators corresponding to the best period of psychological functioning and the current level of psychological functioning of the current patient comprises:

(a) altering the indicators of the current patient; and (b) predicting at least one future level of psychological functioning and the psychiatric symptoms and assets of the current patient as the altered indicators.

18. The method of claim 12, wherein altering the indicators corresponding to the best period of psychological functioning and the current level of psychological functioning of the current patient comprises inflating the indicators the current patient.

19. The method of claim 12, wherein altering the indicators corresponding to the best period of psychological functioning and the current level of psychological functioning of the current patient comprises deflating the indicators of the current patient.

20. The method of claim 12, further comprising a step of graphically representing at least some of the indicators corresponding to the rated responses of the best period of psychological functioning of the patient and the current level of psychological functioning.

21. The method of claim 12, further comprising upon subsequent examinations of the current patient repeating steps (e)–(g).

22. The method of claim 21, further comprising analyzing the indicators corresponding to the current level of psychological functioning.

23. The method of claim 22, further comprising adding the indicators corresponding to the current level of psychological functioning to the profile of the current patient.

24. The method of claim 21, further comprising the repetition of step (j) in claim 14.

25. The method of claim 21, further comprising graphically representing at least some of the indicators corresponding to the analysis of the best period of psychological functioning and the three most recent examinations of psychological functioning.

26. The method of claim 21, further comprising a step where steps (l)–(n) are repeated.

27. The method of claim 12, further comprising a step of graphically representing at least some of the indicators corresponding to the rated responses of the best period of psychological functioning of the patient and the three most recent examinations of psychological functioning.

* * * * *